(12) United States Patent
Klein

(10) Patent No.: US 10,149,915 B1
(45) Date of Patent: Dec. 11, 2018

(54) ULTRAVIOLET LIGHT DISINFECTING—NECTAR TYPE BIRD FEEDER(S)

(71) Applicant: Arnold Gregory Klein, Sandia Park, NM (US)

(72) Inventor: Arnold Gregory Klein, Sandia Park, NM (US)

( * ) Notice: Subject to any disclaimer, the term of this patent is extended or adjusted under 35 U.S.C. 154(b) by 0 days.

(21) Appl. No.: 15/732,797

(22) Filed: Jan. 2, 2018

(51) Int. Cl.
    *A61L 2/10*     (2006.01)
    *A61L 2/26*     (2006.01)
    *A01K 39/01*     (2006.01)

(52) U.S. Cl.
    CPC ............... *A61L 2/10* (2013.01); *A01K 39/01* (2013.01); *A61L 2/26* (2013.01); *A61L 2202/11* (2013.01)

(58) Field of Classification Search
    CPC ........... A61L 2/10; A61L 2/26; A61L 2202/11
    See application file for complete search history.

(56) References Cited

U.S. PATENT DOCUMENTS

| | | | | |
|---|---|---|---|---|
| 3,540,145 A * | 11/1970 | McEwen | ................ | A01M 1/04 43/113 |
| 5,229,053 A * | 7/1993 | Steinberg | ............. | A01K 63/006 264/160 |
| 5,413,069 A * | 5/1995 | Currie | .................. | A01K 39/012 119/52.2 |
| 6,340,824 B1 * | 1/2002 | Komoto | ................ | H01L 33/507 257/100 |
| 7,162,975 B1 * | 1/2007 | Nauert | ................. | A01K 39/014 119/72 |
| 9,192,148 B1 * | 11/2015 | Hill | ...................... | A01K 39/0206 |
| 9,694,094 B1 * | 7/2017 | Wedding | ................. | A61L 2/088 |
| 2003/0173525 A1 * | 9/2003 | Seville | .............. | G01N 21/6428 250/458.1 |
| 2005/0034677 A1 * | 2/2005 | Blake | ................... | A01K 63/006 119/266 |
| 2006/0118055 A1 * | 6/2006 | Kuelbs | ................... | A01K 39/00 119/57.8 |
| 2006/0271340 A1 * | 11/2006 | Levine | ................... | A01K 63/06 702/188 |
| 2007/0221133 A1 * | 9/2007 | Richmond | ........... | A01K 39/012 119/72 |
| 2007/0277742 A1 * | 12/2007 | Venezia | ............... | A01K 63/003 119/245 |
| 2008/0029035 A1 * | 2/2008 | Gou | ...................... | A01K 39/012 119/52.2 |
| 2008/0316732 A1 * | 12/2008 | Blake | ..................... | A01K 63/06 362/101 |

(Continued)

*Primary Examiner* — Jason McCormack
*Assistant Examiner* — Sean Luck

(57) ABSTRACT

A nectar type bird feeder having an incorporated short-wavelength, ultraviolet light source adapted to illuminate the nectar contents and feeder internal surfaces. The ultraviolet light exposure functioning to significantly retard the growth of nectar spoiling micro-organisms and thereby to significantly extend the nectar freshness or service life. The ultraviolet light source may be built directly into the nectar feeder or configured as an add-on accessory. The preferred embodiment of the nectar feeder, ultraviolet light device will be solar powered and made to cycle on/off automatically. As hummingbirds are adapted to see UV-A light (300 nm-400 nm) the light source may be cycled on/off during the day to make the feeder visually conspicuous and thereby more attractive to the feeding birds.

7 Claims, 8 Drawing Sheets

(56) References Cited

U.S. PATENT DOCUMENTS

| | | | | |
|---|---|---|---|---|
| 2009/0031962 | A1* | 2/2009 | Webber | A01K 39/0113 |
| | | | | 119/57.9 |
| 2009/0293341 | A1* | 12/2009 | Fleming | A01M 1/04 |
| | | | | 43/113 |
| 2011/0011345 | A1* | 1/2011 | LoRocco | A01K 39/02 |
| | | | | 119/72 |
| 2014/0224182 | A1* | 8/2014 | Blake | A01K 67/0331 |
| | | | | 119/267 |
| 2015/0059228 | A1* | 3/2015 | Holmes | A01M 31/06 |
| | | | | 43/3 |
| 2016/0058035 | A1* | 3/2016 | McWilliams | A23K 10/20 |
| | | | | 426/1 |
| 2016/0305622 | A1* | 10/2016 | Baker, Jr. | A01K 39/00 |
| 2016/0349433 | A1* | 12/2016 | Donahue | E06B 7/28 |

* cited by examiner

US 10,149,915 B1

ULTRAVIOLET LIGHT DISINFECTING—NECTAR TYPE BIRD FEEDER(S)

Applicant claims the benefit of the provisional application Ser. No. 62/600,166 filed on Feb. 15, 2017.

FIELD OF THE INVENTION

The present invention relates to nectar type bird feeder(s) and feeder accessory devices having an incorporated short wavelength ultraviolet light source for disinfecting the sugar water nectar contents of the feeder.

BACKGROUND OF THE INVENTION

The sugar water nectar used in nectar type bird feeders has a limited life, typically spoiling within a few days, particularly in warmer weather conditions. This spoilage is due to the growth of yeasts, molds and bacteria in the nutrient rich sugar water. It is not unusual in very warm conditions for the nectar to become contaminated in just 3 to 4 days. Typically, the nectar used in these feeders will remain fresh for 3 to 5 days depending on the outdoor temperature. Ornithologists usually recommend that to keep the feeding birds safe, the nectar should be replaced every 3 to 4 days. This routine nectar replacement can be expensive and is inconvenient for many bird-feeding consumers. For this reason, there are a number of commercial products available for extending the life or freshness of the sugar water nectar used in nectar type hummingbird, oriole and butterfly feeders. These products use preservatives or disinfecting agents (sodium benzoate, copper sulfate, etc.) added directly to the nectar or prepackaged nectar preparations. Many Ornithologists have warned consumers against using these nectar-extending products, advising that these chemical additives may cause long term health problems by disrupting the microbiota that live symbiotically with the birds. There is then, a real need for a non-chemical means to extend the service life of the sugar-water used in these nectar type bird feeders.

The instant invention solves the particular problem of nectar spoilage with these nectar feeders by using an incorporated short wavelength ultraviolet light source to sterilize and thereby extend the service life the nectar. This sterilization is achieved using the short wavelength, ultraviolet light source, specifically adapted to illuminate the nectar and nectar feeder interior.

BRIEF DESCRIPTION OF THE DRAWINGS

The following drawings are intended to demonstrate a number of the features and configurations of the ULTRAVIOLET LIGHT DISINFECTING—NECTAR TYPE BIRD FEEDER(S) might have. They are not intended to show all of the device features or design embodiments.

INVENTION DESCRIPTION

Figure 8:
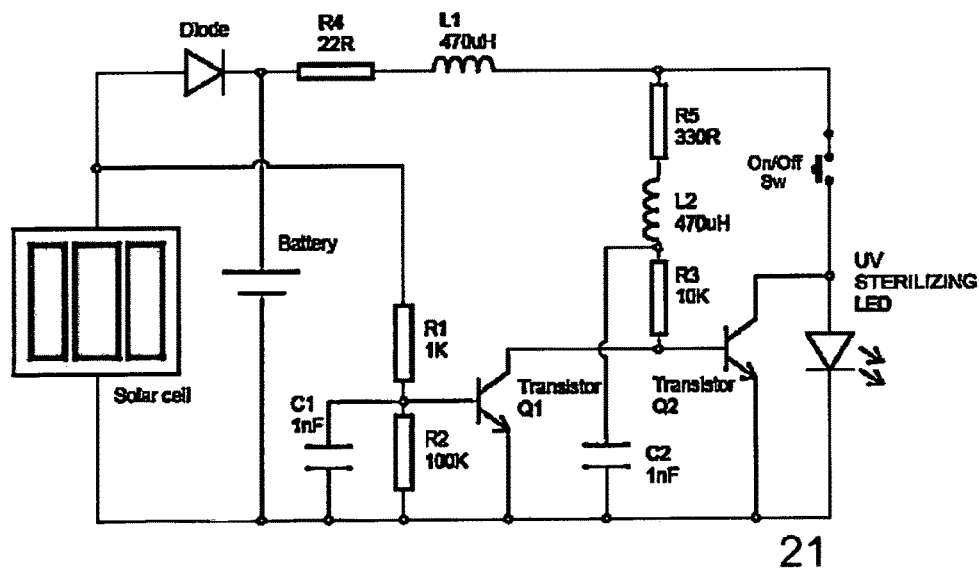
FIG. 8 depicts an electrical schematic diagram for the solar powered ultraviolet light source.
Figure 8:
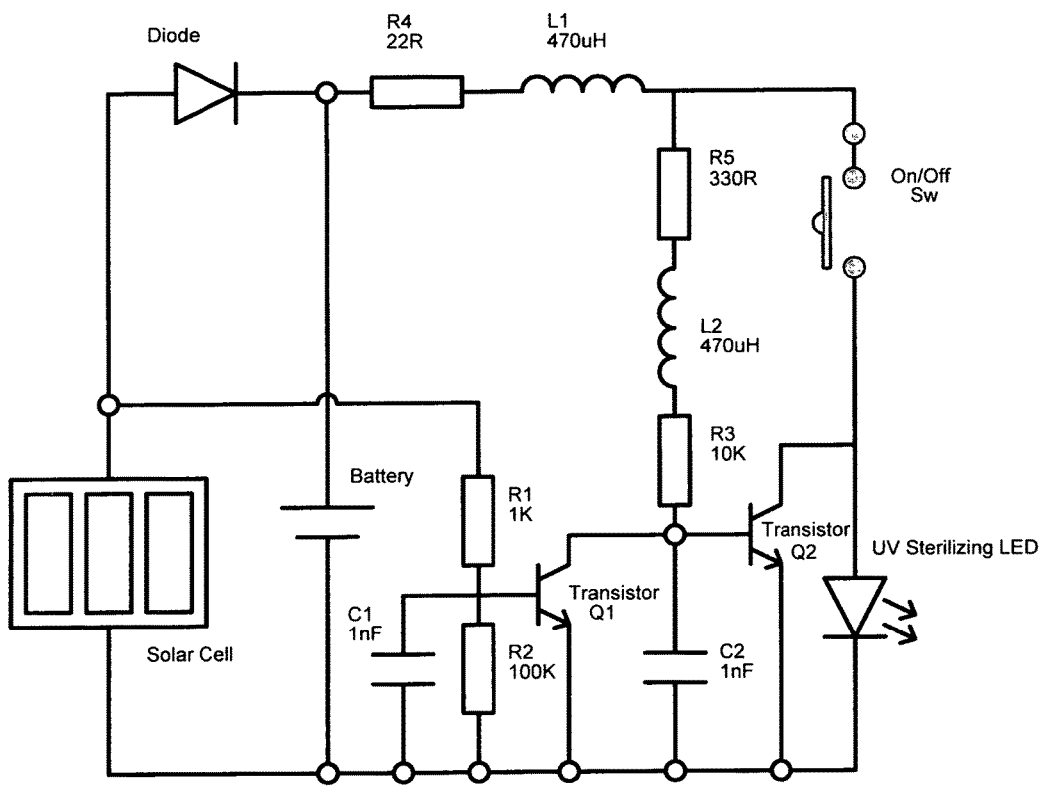

The instant invention combines a simple sterilizing wavelength ultraviolet light source adapted to "shine" on the nectar contents of a nectar type bird feeder. The "sterilizing" ultraviolet light source may be powered using a battery or outlet, or an incorporated solar cell/battery system, very similar in operation to the widely available, low cost, solar powered landscape lighting devices. The FIG. 8 shows the electrical schematic diagram for the typical solar powered landscape light. The essential difference being the use of a sterilizing wavelength, ultraviolet light source LED or lamp used in place of a visible light wavelength or colored LED. There are now, even some solar powered nectar feeder lighting devices that are adapted to turn on during the nighttime hours. These devices are designed for ornamental purposes only and they do not make use of a sterilizing wavelength ultraviolet light source. While these feeders are aesthetically appealing, they have no functionality to "sterilize" and thereby extend the life of the sugar water nectar. The short ultraviolet light illumination of the nectar and internal feeder surfaces acts to retard the growth, development and reproduction of nectar spoiling micro-organisms.

The use of shorter wave ultraviolet light to sterilize instruments, surfaces and even water is well known in the art. Typically these devices use a high intensity, short wavelength ultraviolet light in the UV C (200 nm-280 nm) and UV B (280 nm-315 nm) wavelengths. These high-energy devices are very effective in their disruption of the DNA of micro-organisms. This disruption prevents these micro-organisms (bacteria, molds and fungus) from multiplying (reproducing). Of course, there is nothing preventing the use of UV-C or UV-B to be used to sterilize the nectar, but it may turn out to be more economical and in some ways preferable to consumers to use a longer term UV-A ("blacklight" 315 nm-400 nm) exposure. Typically, UV-A is not used for sterilization, but it has been shown to have significant sterilization effects up to wavelengths as high as 385 nm (reference the study at the internet link: https://www.google.com/search?q=365+nm+for+sterilization&ie=utf-8&oe=utf-8). The UV-A ultraviolet light takes longer to sterilize, but this is not a problem as the exposure can extend through an entire night. Some further experimentation and consumer preference surveys will be required to optimize the ultraviolet light source(s), electrical power and exposure time/schedule for the instant invention. Since the nectar starts out sterile or nearly sterile, the ultraviolet light only needs to inhibit microbial growth. Most feeder consumers would be very happy with a product that reliably extends the nectar freshness in their feeders by 2×-3× or up to one week or 10 days. Testing has shown the ultraviolet light exposed nectar can remain "fresh" for up to two weeks.

Figure 1:
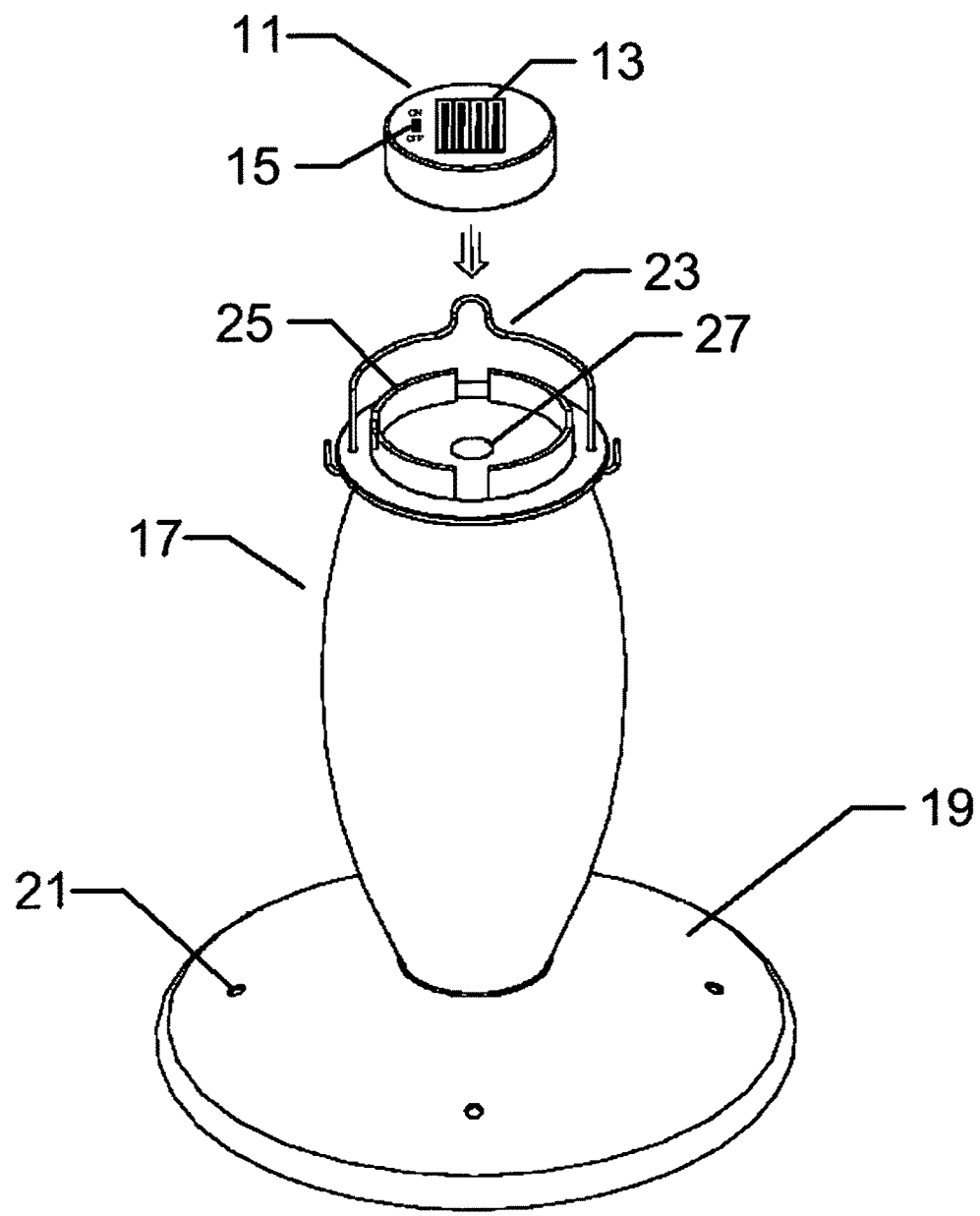
FIG. 1 depicts a slightly rotated and exploded top view of the ultraviolet light source and the nectar type bird feeder.

The FIG. 1 shows a solar-powered 13 ultraviolet sterilizing light assembly 11 adapted to be securely positioned as shown at 25 on the top of a nectar type bird feeder 17. This nectar type bird feeder 17 has a lower reservoir 19 and feeding ports 21. The nectar feeder 17 is hung using the hanger at 23. The feeder top surface may have an incorporated aperture as shown at 27 to allow the ultraviolet light to enter the feeder. Many of the upper portion of these nectar type bird feeders are made of glass which will transmit most UV-A light. In the event that shorter wavelength ultraviolet light sources (UV-C) are used, this aperture may be made of a material that transmits shorter wavelength ultraviolet light. Finally, although it is not essential, the ultraviolet light assembly 11 may have an incorporated on/off switch as shown at 15.

Figure 2:
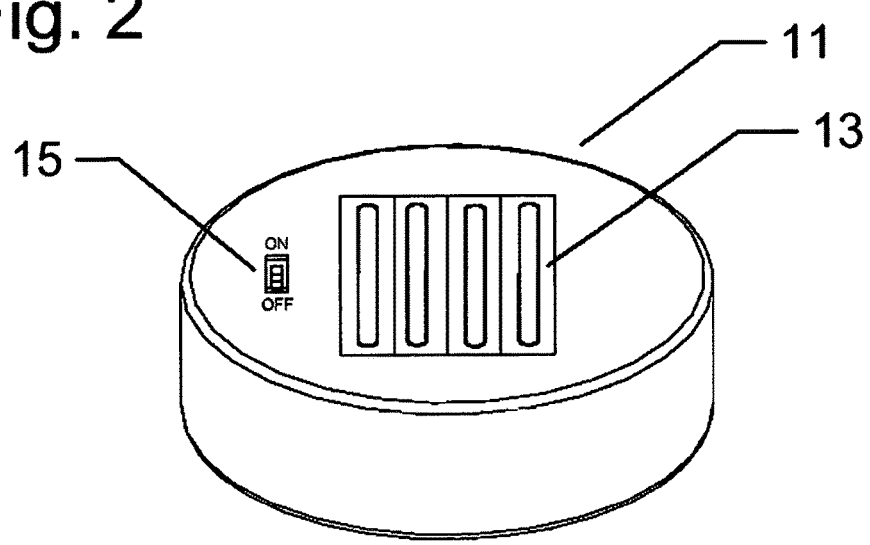
FIG. 2 depicts an enlarged, slightly rotated top view of the ultraviolet light source.
Figure 3:
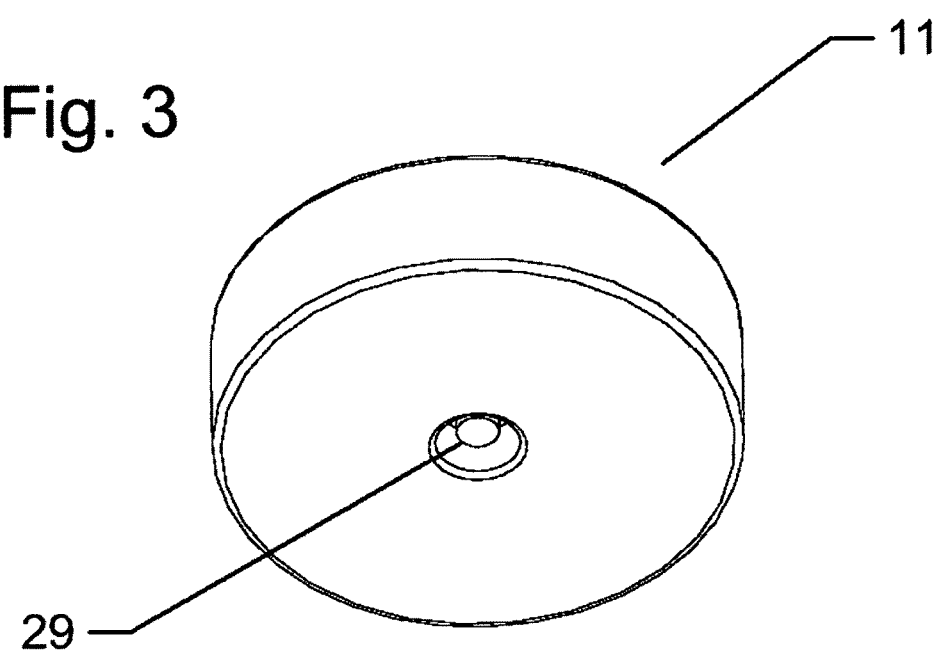
FIG. 3 depicts an enlarged, slightly rotated bottom view of the ultraviolet light source.

The FIGS. 2 and 3 are enlarged views of the ultraviolet light assembly 11 showing the ultraviolet light source at 29. The FIG. 3 shows a LED type ultraviolet light source at 29, but any specifically adapted ultraviolet light source may be used.

Figure 4:
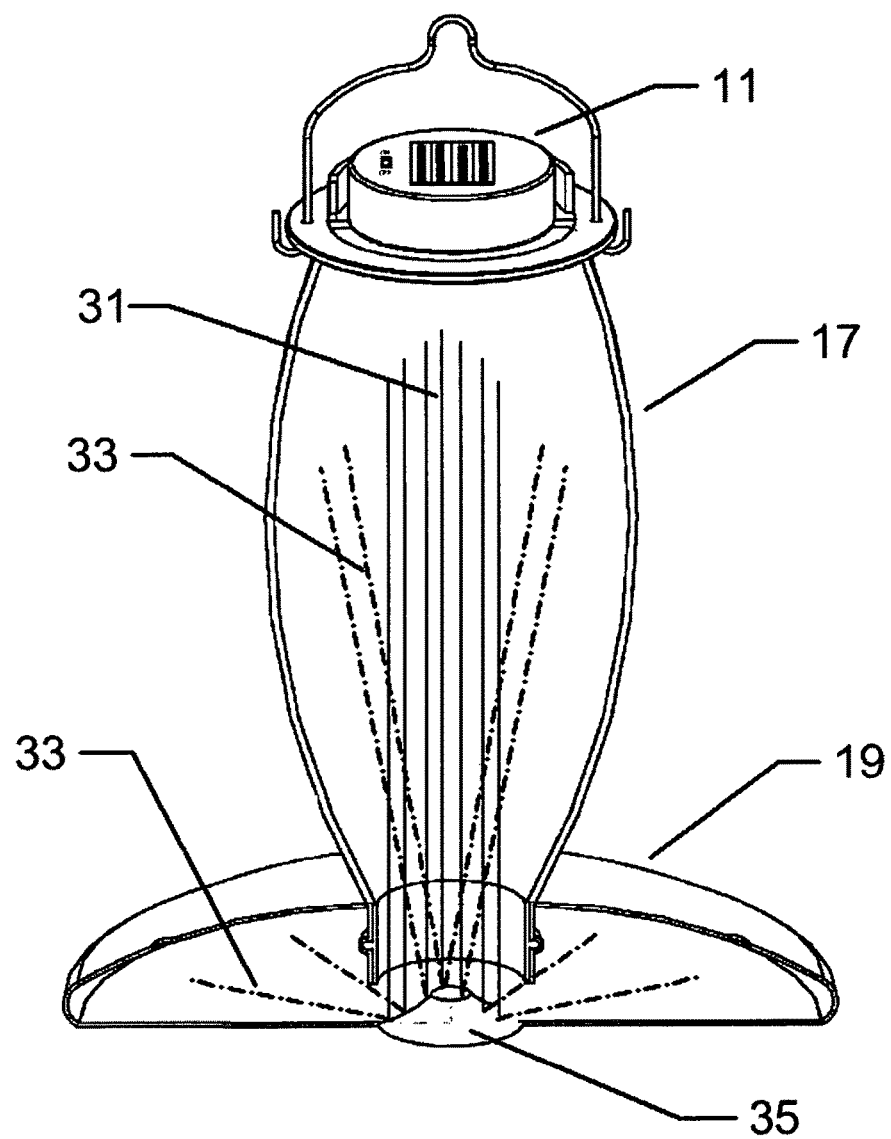
FIG. 4 depicts a partial cutaway view of the nectar feeder with incorporated ultraviolet light source.

Referring to FIG. 4 there is shown a nectar type bird feeder 17 with lower reservoir 19. The FIG. 4 shows the incoming ultraviolet light with unbroken lines at 31 and the reflected light 33 that is directed back into the lower reservoir 19 and feeder 17 by the reflector shown at 35. This reflector 35 is configured to direct some of the sterilizing ultraviolet light into the lower reservoir 19 and feeder 17. There are typically many light lens types available for controlling the light dispersion from an LED source. It is then relatively straightforward to optimize the dispersion of the ultraviolet light for sterilizing the nectar and feeder interior surfaces.

Figure 5:
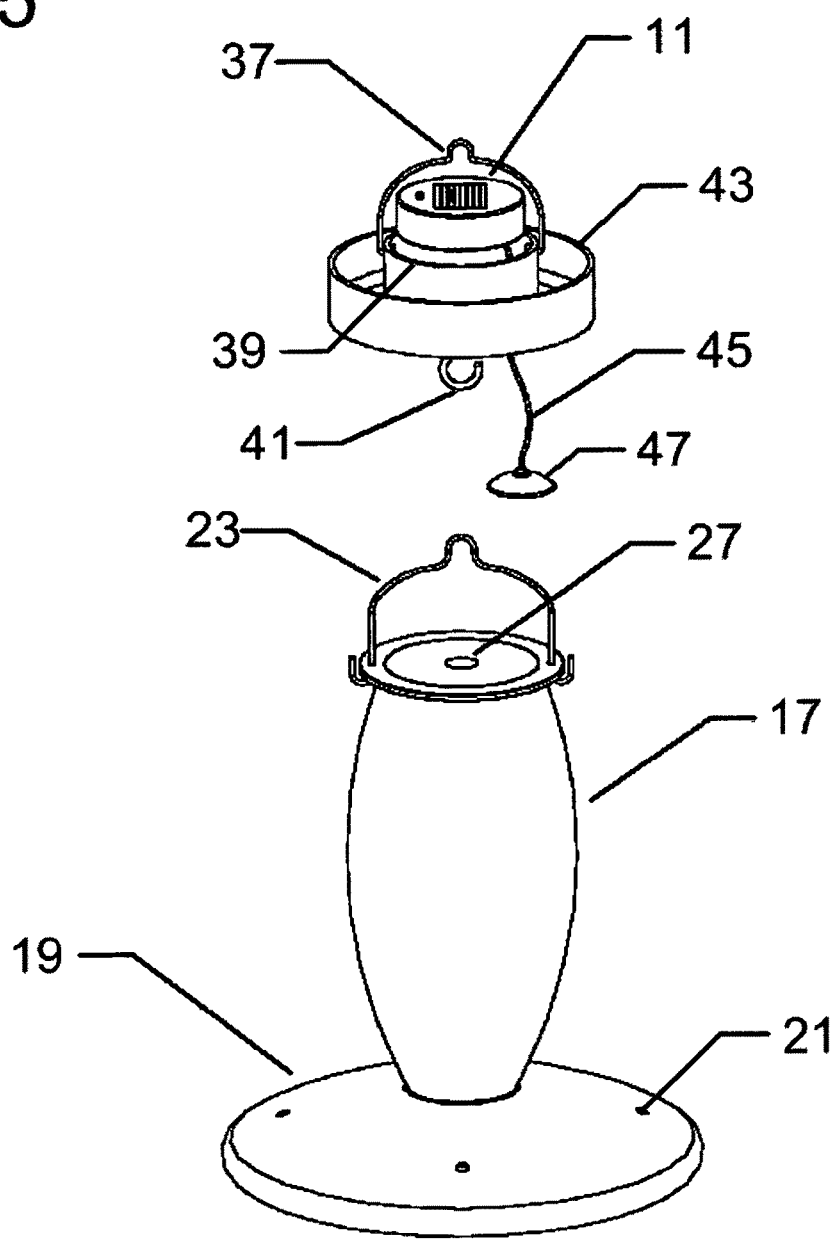
FIG. 5 depicts an exploded view of a stand alone ultraviolet light source and nectar feeder assembly.
Figure 6:
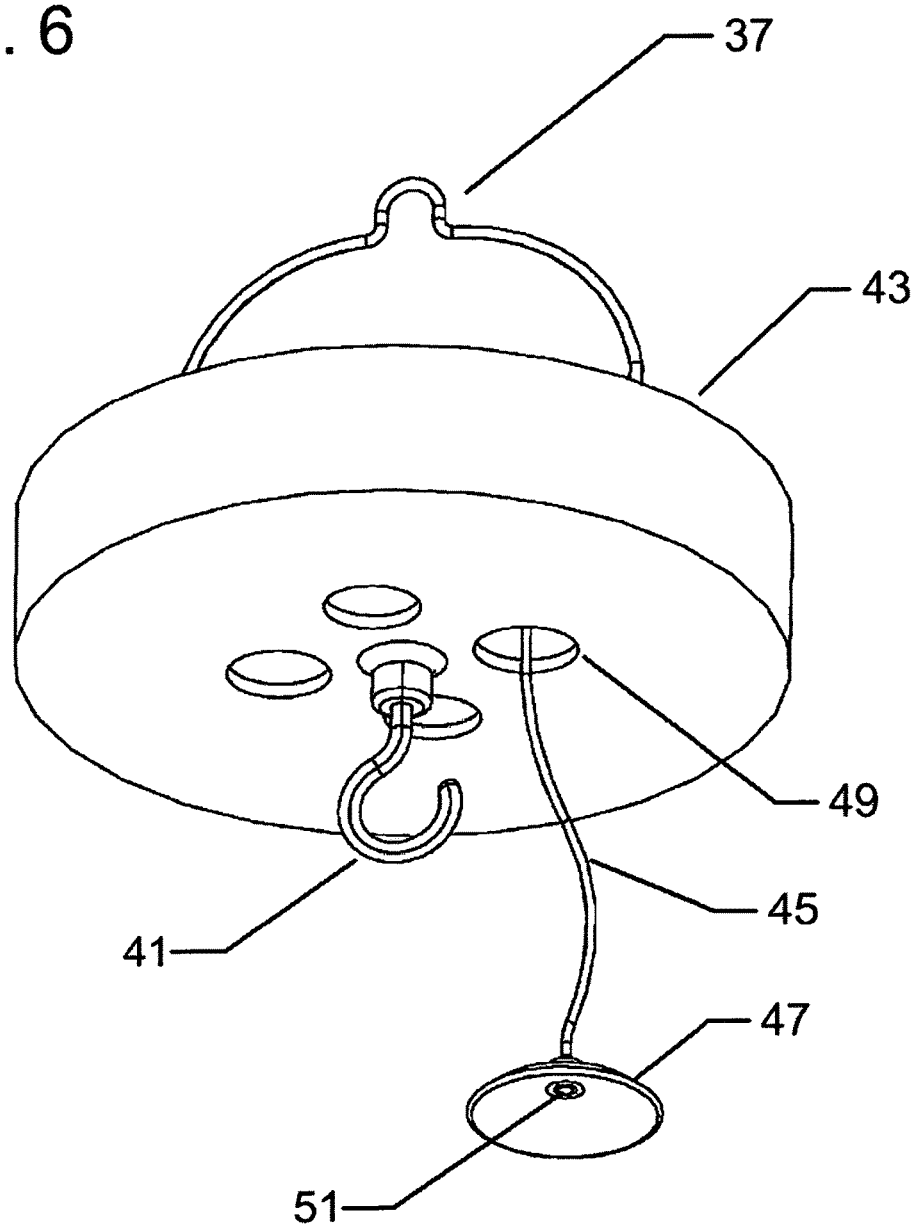
FIG. 6 depicts an enlarged, slightly rotated bottom view of a stand alone, ultraviolet light source.
Figure 7:
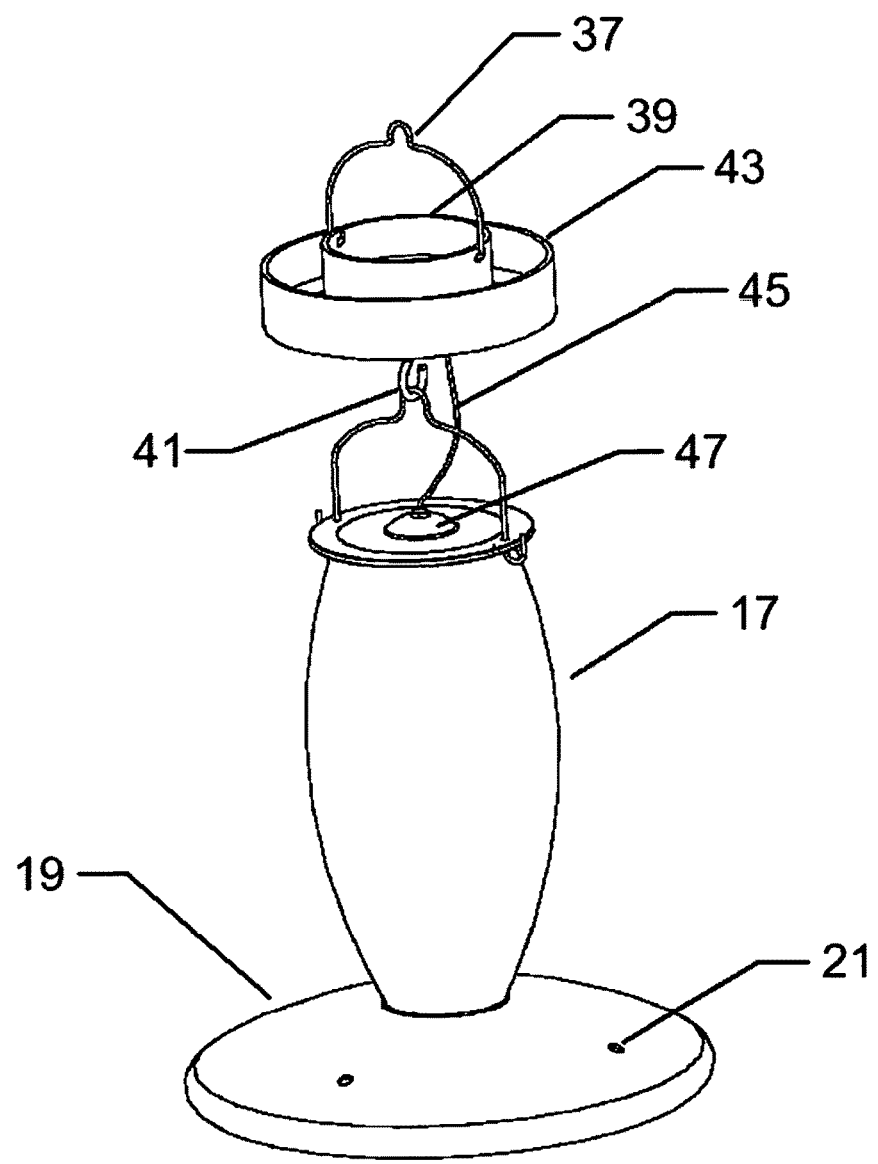
FIG. 7 depicts a stand alone, ultraviolet light source attached to a nectar feeder assembly.

Referring to FIGS. 5 through 7 there is shown a water moat 43 adapted at 39 to hold an ultraviolet light source assembly 11 to be used with nectar feeders not specifically adapted for ultraviolet light sterilization. The water moat 43 has an upper hanging bail 37 and a lower nectar feeder hanging hook 41. The ultraviolet light LED 51 is connected by a power cord 45 and routed through a port 49 where it is held on the feeder 17 using a suction cup 47.

Referring to FIG. 8 there is shown an electrical schematic for the ultraviolet light source. This circuit may also incorporate a capacitor for jump starting or providing a higher voltage to the ultraviolet light source. The electrical control circuit will require modification depending on the ultraviolet light source and associated U V wavelength. There is also some opportunity to optimize the nectar sterilization by selectively scheduling the ultraviolet exposure through the daytime or night. While the preferred embodiment of the ultraviolet light source uses a solar panel and rechargeable battery, an external electrical energy source (power cord) could be used.

It should be noted that there are a wide variety of nectar feeders and feeder designs that are commercially available. Although not shown in the patent figures, many of these feeders are of a bowl type configuration. These bowl type feeders do not rely on vacuum to hold their nectar contents. Because of this, the UV light source may be located on the top, or integrally incorporated into the top of these feeders without any concern for maintaining a vacuum seal. This bowl feeder configuration allows for the direct transmission of the ultraviolet light source directly onto the nectar contents without any concern for light transmission losses. Since the shorter wavelength UV-C and UV-B light does not penetrate most glass or most clear plastics, it will be reflected within the interior of the feeder, thus minimizing any exposure risk to the consumer or the feeding birds.

The invention embodiments shown in the patent figures are designed to directly expose the feeder contents (nectar) and feeder interior to the disinfecting UV light source. It is technically feasible to add a small pump element to a feeder wherein the nectar is periodically cycled through an ultraviolet illuminated chamber where it is exposed to a more localized source of disinfecting UV light. A feeder constructed with these additional elements may well keep the nectar fresh for an extended period, but this type of configuration would be more expensive to manufacture and would require a more involved cleaning procedure when the nectar is to be replaced.

Also, while the ultraviolet light source is intended to inhibit the growth, development and reproduction of (nectar spoiling) microbes and thereby to extend the limited life of the sugar water nectar, there is an opportunity to enhance the feeder esthetics by decorating the feeder using fluorescing type pigments. The UV-A light source is essentially similar in wavelength to the "black" lights that are widely used to make fluorescent pigments appear to glow. It is possible then to decorate the feeder and feeder ports (exterior or interior) using fluorescing pigments that will appear to "glow" when exposed to the ultraviolet light. Since the "sterilizing" UV light may not always be in the visible range, it will be easy for the consumer to detect the operation of the UV light source using a fluorescing pigment colored or molded indicator.

Finally, it has been discovered that hummingbirds are adapted to see some wavelengths (approximately 300 nm to 400 nm) of UV light that are not visible to humans. Since many flowers reflect UV light, this is likely to be an adaptation that helps the birds to locate nectar sources. If the ultraviolet light source is cycled on during the day, the nectar feeders employing this UV sterilizing technology may be made conspicuously visible and thereby more attractive to the feeding birds.

I have now described my invention in considerable detail, however others skilled in the art can devise and develop alternate and equivalent constructions. Hence, I desire my protection not to be limited by the constructions illustrated and described, but only by the proper scope of the appended claims.

I claim:

1. An apparatus comprising:
    a nectar type bird feeder comprising nectar and an ultraviolet light source configured to emit sterilizing ultraviolet light,
    wherein the ultraviolet light source is adapted to illuminate and sterilize the internal surfaces of the nectar type bird feeder and the nectar.

2. The apparatus of claim 1, wherein the ultraviolet light source is adapted to illuminate the internal surfaces of the nectar feeder.

3. The apparatus of claim 1, wherein the ultraviolet light source comprises an external energy source or incorporated battery.

4. The apparatus of claim 1, wherein the ultraviolet light source is integrally incorporated into the nectar type bird feeder.

5. The apparatus of claim 1, wherein the ultraviolet light source comprises an incorporated solar power panel adapted to recharge a battery.

6. The apparatus of claim 1, wherein the apparatus comprises fluorescing pigments that glow when exposed to ultraviolet light.

7. The apparatus of claim 1, wherein the ultraviolet light source is cycled on during the daylight hours to attract feeding birds.

* * * * *